United States Patent
Luo et al.

(10) Patent No.: US 7,455,861 B2
(45) Date of Patent: Nov. 25, 2008

(54) ANGELICAE SINENSIS EXTRACTS USEFUL FOR TREATMENT OF CANCERS

(75) Inventors: Jiann-Kuan Luo, Temple Terrace, FL (US); Horng-Jyh Harn, Taipei (TW); Wen-Liang Chang, Taipei (TW); Shinn-Zong Lin, Taipei (TW); Yeung-Leung Cheng, Taipei (TW); Nu-Man Tsai, Shiu Township, Changhua County (TW)

(73) Assignee: Buddhist Tzu Chi General Hospital, Haulien (TW)

( * ) Notice: Subject to any disclaimer, the term of this patent is extended or adjusted under 35 U.S.C. 154(b) by 0 days.

(21) Appl. No.: 11/561,713

(22) Filed: Nov. 20, 2006

(65) Prior Publication Data
US 2007/0134351 A1 Jun. 14, 2007

Related U.S. Application Data

(62) Division of application No. 11/246,009, filed on Oct. 7, 2005, now abandoned.

(60) Provisional application No. 60/616,636, filed on Oct. 8, 2004.

(51) Int. Cl.
*A61K 36/00* (2006.01)
*A61K 125/00* (2006.01)

(52) U.S. Cl. ..................... 424/725; 424/773
(58) Field of Classification Search ............... None
See application file for complete search history.

(56) References Cited

U.S. PATENT DOCUMENTS 4,613,591 A * 9/1986 Aburada et al. ............... 514/34

OTHER PUBLICATIONS

Cheng et al. : Acetone Extract Of Angelica Sinensis Inhibits Proliferation Of Human Cancer Cells Via Inducing Cell Cycle Arrest And Apoptosis. Life Sciences.: vol. 75. Issue 13. 2004. pp. 1579-1596.*
Bello et al.: Low-Dose Chemotherapy Combined With An Antiangiogenic Drug Reduces Human Glioma Growth In Vivo.: Cancer Research.: 61. 2001. pp. 7501-7506.*
Hamer et al.: The Genomic Profile Of Human Malignant Glioma Is Altered Early In Primary Cell Culture And Preserved In Spheroids.: Oncogene.: 2007. pp. 1-6.*

* cited by examiner

*Primary Examiner*—Patricia Leith
*Assistant Examiner*—Melenie McCormick
(74) *Attorney, Agent, or Firm*—Panitch Schwarze Belisario & Nadel LLP

(57) ABSTRACT

The invention provides an acetone extract, chloroform extract or hexane extract of *Angelicae sinensis* and/or the active components purified therefrom, such as n-butylidenephthalide, which are effective in treating cancers.

3 Claims, 17 Drawing Sheets

T-Test: *, P-value<0.05; , P-value<0.005; *, P-value<0.0001

*: $p<0.05$; **: $p<0.005$

ANGELICAE SINENSIS EXTRACTS USEFUL FOR TREATMENT OF CANCERS

CROSS-REFERENCE TO RELATED APPLICATIONS

This is a divisional application of U.S. patent application Ser. No. 11/246,009, filed Oct. 7, 2005, which claims the benefit of U.S. Provisional Application No. 60/616,636, filed Oct. 8, 2004, the contents of each of which are incorporated herein by reference.

BACKGROUND OF THE INVENTION

The invention mainly relates to a new use of an acetone extract, chloroform extract or hexane extract of *Angelicae sinensis* and the active components purified therefrom in the treatment of cancers.

Cancers are abnormal cell proliferations that result from the accumulation of genetic changes in cells endowed with proliferative potential. Treatment of cancers has relied mainly on surgery, chemotherapy, radiotherapy and more recently immunotherapy. However, new approaches for treating and preventing cancers are still desired.

*Angelicae sinensis* (Dangqui) is one of the most frequently occurring drugs in the prescriptions of traditional Chinese medicines. The traditional uses of *Angelicae sinensis* include those to promote blood production, protect liver, lower blood pressure, kill bacteria, ease pain mostly for menstrual disorder in women, and lower cholesterol (Chinese Herbs, Shanghai Science and Technology Publication, Inc., Shanghai, China, Vol. 5, p. 893, 1999).

CN1053747 disclosed that *Angelicae sinensis* (Oliv) Diels, ASD, and the ASDP and ASDE as effective components of an adjuvant was prepared, and could be used as an immunological adjuvant to genetically-engineered hepatitis B vaccines. It was reported in CN1109356 that the effective component, lactones (ASDE), extracted from *Angelicae sinensis* (oliv) diels, ASD, could be used as an immunological adjuvant, which can enhance the immunogenicity and help lower toxicity. Kumazawa et al. provided immunostimulating polysaccharides separated from a hot water extract of *Angelicae sinensis*, which could be used as a potent adjuvant for its anti-tumor activity as observed in the prolongation of the survival period of mice bearing Ehrlich ascites cells (Y. Kumazawa, et al., Immunology, Vol. 47, p. 75, 1982). However, this prior art reference provides only a general description of the treatment of cancers with the polysaccharides separated from *Angelicae sinensis* through their immunostimulating activity, without sufficient evidence regarding the mechanism.

BRIEF SUMMARY OF THE INVENTION

This invention provides that an acetone extract, chloroform extract or hexane extract of *Angelicae sinensis*, or at least one component purified therefrom, such as n-butylidenephthalide (BP), can also inhibit telomerase activity of cancer cells and further induce their apoptosis so that they can be used to treat malignant neoplasms. Therefore, an acetone extract, chloroform extract or hexane extract of *Angelicae sinensis*, and the components purified therefrom, such as n-butylidenephthalide, are potent for manufacturing of medicines for the treatment of cancers, and can be used in combination with chemotherapy drugs through their activities on cell cycle regulation, and telomerase inhibition.

Accordingly, one object of the present invention is to provide a method for inhibiting cancer cell proliferation and migration in tumor tissues.

Another object of the present invention is to provide a method for inhibiting telomerase activity of cancer cells.

Yet another object of the present invention is to provide a method for inducing apoptosis of cancer cells.

Another object of the present invention is to provide the use of an acetone extract, chloroform extract or hexane extract of *Angelicae sinensis*, or at least one component purified therefrom, such as n-butylidenephthalide, for manufacturing medicine for the treatment of cancer, and as an adjuvant in combination with chemotherapy drugs through their activities on cell cycle regulation and/or telomerase inhibition.

BRIEF DESCRIPTION OF THE SEVERAL VIEWS OF THE DRAWINGS

The foregoing summary, as well as the following detailed description of the invention, will be better understood when read in conjunction with the appended drawings relating to embodiments which are presently preferred. It should be understood, however, that the invention is not limited to the precise embodiments shown.

In the drawings.

DETAILED DESCRIPTION OF THE INVENTION

Figure 1A:
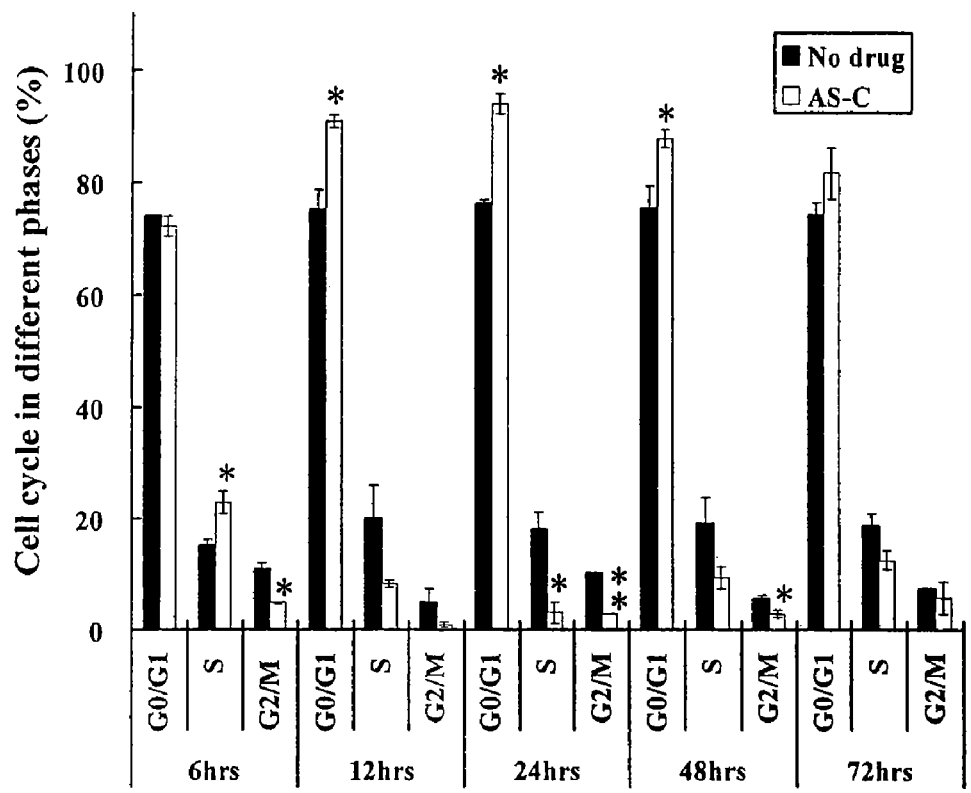
FIG. 1a provides the results of the cell cycle analysis, which demonstrates that treatment with 70 μg/ml AS-C (the chloroform extract of *Angelicae sinensis*) enhanced cell cycle accumulation at G0/G1 phase (>90%) in GBM cells (DB-TRG-05M) (*$p<0.05$) with a concurrent decrease in S phase. The results on G5T/VGH were about the same and not shown in the graph.

This invention provides that the organic solvent extracts of *Angelicae sinensis*, or the components purified therefrom, such as n-butylidenephthalide (BP), can inhibit telomerase activity of cancer cells and further induce their apoptosis. Therefore, they can inhibit cancer cell proliferation and can be used to treat cancers.

Preparation of *Angelicae sinensis* Extracts

*Angelicae sinensis* (Dangqui) has long been used in blood diseases and female diseases. Normally, the dried root of *Angelica sinensis* (Oliv.) Diels, belonging to the family of Umbelliferae, is used. *Angelica sinensis* (AS) is appreciated by those skilled in this art. A variety of techniques are well known in the art for extracting, separating, and/or purifying individual active components of *Angelicae sinensis*. The organic solvent extracts of *Angelicae sinensis* may be obtained by any standard procedures commonly used in the field. According to the invention, *Angelicae sinensis* is extracted with acetone, chloroform, or hexanes. In one embodiment of the invention, the dried and powdered rhizomes of *Angelicae sinensis* were extracted with acetone as a solvent to give an extract as AS-A. Furthermore, AS-A was further extracted with chloroform to give an extract as AS-C; and AS-A was further extracted with hexanes to give an extract as AS-H.

Purification of Active Components

Active components of *Angelicae sinensis* may be isolated and/or purified from the organic solvent extracts of *Angelicae sinensis* by using any techniques known in the art. The active components may be purified from *Angelicae sinensis* in any form, particularly the rhizomes. Various techniques that may be employed in the further purification include filtration, selective precipitation, extraction with organic solvents, extraction with aqueous solvents, column chromatography, high performance liquid chromatography (HPLC), etc. According to the invention, some active components were purified from the organic solvent extracts of *Angelicae sinensis*, such as ligustilide and n-butylidenephthalide, which can induce tumor cell apoptosis. In one embodiment of the invention, E- and Z-geometrical isomers of n-butylidenephthalide (BP) were separated with column chromatography and characterized with HPLC and NMR.

Mechanisms of Cancer Treatment

Telomeres, the extremities of eukaryotic chromosomes, are essential for maintaining the integrity of the genome and are a key determinant of cellular aging and immortality (N. W. Kim, M. A. Piatyszek, K. R. Prowse, C. B. Harley, M. D. West, P. L. C. Ho, G. M. Coviello, W. E. Wright, S. L. Weinrich, J. W. Shay, Science, 266, 2011-2015 (1994)). Telomere length and the rate of its reduction vary among organs and individuals. Large interchromosomal variation in telomere length exists in mice and humans and an aberration of a telomere in a single chromosome can lead to abnormal chromosomal segregation (L. L. Sandell, V. A. Zakian, Cell, 75, 729-739 (1993)). Therefore, it is concluded that the regulation and maintenance of telomere length variation play an important role in cancer development. Apparently cells have a system to protect against both critical shortening and abnormal elongation of the telomere. Telomerase has been identified as one of the telomere length regulators (G. B. Morin, Cell, 59, 521-529 (1989)). Hence, any compound or substance having a selective inhibiting telomerase activity can inhibit tumor cell growth and thus further induce cell apoptosis of tumor cells.

Apoptosis is another mechanism of cancer therapy, which has become one of the newest areas of cell biology research. The activation of the apoptosis program is regulated by various signals from both intracellular and extracellular stimuli. Indeed, in recent years evidence is beginning to accumulate that many (and perhaps all) agents of cancer chemotherapy kill tumour cells by launching the mechanisms of apoptosis. New drugs associated with apoptosis are expected to be most effective against tumours with high proliferation rates. Many such candidates are being screened for use in the treatment of cancer (Ricardo Pérez-Tomás, Beatriz Montaner, Esther Llagostera, Vanessa Soto-Cerrato, Biochemical Pharmacology, 66, 1447-1452 (2003)).

Apoptosis is monitored by the analysis of two commonly used endpoints-the morphological changes of cells (condensation of nuclear chromatin, formation of apoptotic bodies) and DNA fragmentation into large fragments (300 and 50 kbp) and then to oligonucleosomesized fragments (multiples of 200 bp), which appear as a "ladder" of DNA bands upon agarose gel electrophoresis. Although observation of these endpoints is an indicator of apoptosis, quantification of the percentage of apoptotic cells in a population by such an assay is impossible. For this purpose, we also used the TUNEL assay during which fluorescently-biotinylated nucleotides were added to the ends of DNA fragments within fixed cells (Jacques Piettea, Cédric Volantia, Annelies Vantieghemb, Jean-Yves Yvette Habrakena, Patrizia Agostinis, Biochemical Pharmacology, 66, 1651-1659 (2003)).

The relative contribution of the receptor and the mitochondrial pathways to drug-induced apoptosis has been a subject of controversy. It depends on the type of the cytotoxic drug itself, the dose and kinetics or on differences between certain cell types, which affects the cell type dependent signaling in the Fas/FasL pathway.

Apoptosis pathways can be initiated through different sites, such as the plasma membrane, by way of death receptor mediated signaling (receptor pathway; Fas/FasL/caspase-8/caspase-3 pathway), the mitochondria (mitochondrial pathway; Bax/AIF/caspase-9/caspase-3 pathway), and cell cycle regulation (including p53, Rb tumor suppressors, p16 and p21 cyclin kinase inhibitors and cyclin/cdk cell cycle check points) (Simone Fulda, Matroulea, Klaus-Micheal Debatin, Cancer Letter, 197, 131-135 (2003)).

It has been reported in the literature that acetone extract, chloroform extract or hexane extract of *Angelicae sinensis* and its active components have anti-angina, anti-agglutination and certain other activities on the cardiovascular system.

Surprisingly, we found in this invention that the acetone extract, chloroform extract or hexane extract of *Angelicae sinensis*, and the active components purified therefrom, such as n-butylidenephthalide, have anti-cancer activities.

According to this invention, the growth of several cancer cell lines were tested against the acetone extract, chloroform extract or hexane extract of *Angelicae sinensis*, the active components purified therefrom, such as n-butylidenephthalide. It was found that they were cytotoxic to cancer cells; they inhibited telomerase activity of cancer cells (as shown in Example 7); they suppressed cancer cell proliferation (as shown in Example 2) and they also induced cancer cell apoptosis (as shown in Examples 3 and 4). Furthermore, animal studies also showed they were effective in suppressing cancer growth (as shown in Examples 5 and 6). They are therefore potent for treating cancers, particularly human malignant glioblastoma, colorectal cancer, leukemia, neuroblastoma, hepatoma, breast, ovarian and lung cancers.

Pharmaceutical Compositions

The acetone extract, chloroform extract or hexane extract of *Angelicae sinensis*, active components purified therefrom, and the derivatives according to the present invention may be administered by any conventional route of administration including, but not limited to, oral, parenteral, intraperitoneal (ip), intravenous (iv), intramuscular (im), subcutaneous (sc), pulmonary, transdermal, buccal, nasal, sublingual, ocular, rectal, vaginal or other routes. It will be readily apparent to those skilled in the art that any dosage or frequency of administration that provides the desired therapeutic effect is suitable for use in the present invention. In a preferred embodiment of the invention, they are administered by oral delivery, using methods known to those skilled in the art of drug or food delivery.

For the purposes of therapeutic administration, the acetone extract, chloroform extract or hexane extract of *Angelicae sinensis*, active components purified therefrom, and the derivatives may be in the form of a tablet, pill, capsule, granule, gel, powder, sterile parenteral solution or suspension, metered aerosol or liquid spray, or suppository, depending on the administration route. To prepare a pharmaceutical composition of the present invention, the organic solvent extracts of *Angelicae sinensis*, active components purified therefrom, or the derivatives are admixed with a pharmaceutically acceptable carrier according to conventional pharmaceutical compounding techniques, wherein the carrier may take a wide variety of forms depending on the form of preparation desired for administration. Suitable pharmaceutically acceptable carriers are well known in the art. Descriptions of some pharmaceutically acceptable carriers may be found in *The Hand Book of Pharmaceutical Excipients*, published by the American Pharmaceutical Association and the Pharmaceutical Society of Great Britain. For instance, the tablets, capsules, gels, solutions or suspensions may also include the following components: a pharmaceutically acceptable excipient or carrier, which is a non-toxic, inert solid or semi-solid, diluent, encapsulating material, a gel base or formulation auxiliary of any type. The solutions and suspensions may contain auxiliaries, such as water for injection, saline solution, polyethylene glycols, glycerin, propylene glycol or other synthetic solvents; proteins such as serum albumin to enhance solubility; antibacterial agents such as benzyl alcohol or methyl parabens; antioxidants such as ascorbic acid or sodium bisulfite; buffers such as acetates, citrates or phosphates and agents for the adjustment of tonicity such as sodium chloride or dextrose. The solution or suspension preparations can be enclosed in ampoules, disposable syringes or multiple dose vials made of glass or plastic.

The acetone extract, chloroform extract or hexane extract of *Angelicae sinensis*, active components purified therefrom, and the derivatives according to the present invention may also be administered as an adjuvant in combination with chemotherapy drugs, such as actinomycin, adriamycin, Ara-C, bleomycin, carmustin, cisplatin, cyclophosphamide, daunomycin, mitomycin, taxol, vinblastine, etc.

The acetone extract, chloroform extract or hexane extract of *Angelicae sinensis*, active components purified therefrom, and the derivatives according to the present invention may also be formulated in any dietary compositions by using any techniques known to those skilled in the art.

The following Examples are given for the purpose of illustration only and are not intended to limit the scope of the present invention.

Materials and Methods

Preparation of *Angelicae sinensis* extracts and Compounds

The roots of *Angelicae sinensis* (Oliv.) were supplied from Chung-Yuan Co., Taipei, Taiwan and were identified by Professor Han-Ching Lin. A voucher of herbarium specimen was deposited at the School of Pharmacy, National Defense Medical Center. The dried and powdered rhizomes of *Angelicae sinensis* (12 kg) were extracted 3 times with acetone (24 L/time) to give an acetone extract called AS-A. AS-A was then subjected to chloroform extraction 3 times (24 L/times). The latter extracts were concentrated under reduced pressure to yield 31.67 g of chloroform extract, called AS-C (from 100 g of acetone extract). A hexane extract (AS-H) was obtained by extracting AS-A with hexanes. n-Butylidenephthalide (BP) was purchased from Lancaster Synthesis Ltd. (Newgate, Morecambe, UK) and used without further purification. E- and Z-forms of BP were separated with column chromatography and characterized with HPLC and NMR. They were dissolved in DMSO, incubated with shaking at 25° C. for 1 hour and stored at 4° C. before each in vitro experiment.

Cell Proliferation Assay in vitro

Human umbilical vascular endothelial cells (HUVECs) were purchased from Cascade Biologics, Inc. (USA). HUVECs were maintained in Medium 200 (Cascade Biologics, Inc. USA) supplemented with 10% fetal bovine serum (FBS; Gibco BRL) and low serum growth supplement (LSGS; Cascade Biologics, Inc. USA). Human dermal fibroblasts (HDFs) were purchased from Cascade Biologics, Inc. (USA). HDFs were maintained in Medium 106 (Cascade Biologics, Inc. USA) supplemented with 10% FBS and low serum growth supplement (LSGS; Cascade Biologics, Inc. USA). The human colon adenocarcinoma cell lines HT-29 were purchased from the ATCC (Manassas, Va. USA). HT-29 were maintained in Dubecco's Modified Eagle Medium (DMEM; Gibco) supplemented with 10% FBS and 100 ng/ml penicillin and 100 ng/ml streptomycin (Life Technologies, Inc., Grand Island, N.Y., USA). For the proliferation assay of cell in log growth (G1), the cells were harvested at 60-80% of confluence. 100 µl of cell suspensions were dispensed onto a Falcon 96-well plates The densities were $6 \times 10^3$ cells/well in Medium 200 (for HUVECs), and $9 \times 10^3$ cells/well in Medium 106 (for HDFs), and $5 \times 10^3$ cells/well in DMEM (for HT-29) supplemented with 10% FBS. The cells were pre-incubated for 24 hours in an incubator (Humidified atmosphere, e.g., at 37° C., 5% $CO_2$). 10 µl of toxicant of various concentrations were added into the culture medium of the plate. The cell cultures were incubated for 48 hours. 10 µl of the Cell Counting Kit-8 (CCK-8; DOJINDO) solution were added and the cell cultures incubated for 1~4 hours in the incubator. The absorbance was measured at 450 nm, using a microplate reader with a reference wavelength at 600 nm or over.

Extraction of RNA from HUVECs

Total RNA was isolated from the cultured stromal cells using a modified guanidium isothiocyanate method (Trizol; Invitrogen).

Homogenization: The cells were lysed directly in a 6 well culture plate by adding 1 ml of trizol reagent to a 3.5 cm diameter well, and passing the cell lysate several times through a pipette.

Phase separation: The homogenized samples were incubated for 5 minutes at 15 to 30° C. to permit the complete dissociation of nucleoprotein complexes. Then, 0.2 ml of chloroform (Riedel-de-haën) per 1 ml of trizol reagent was added. Sample tubes were capped securely. The tubes were vigorously shaken by hand for 15 seconds and incubated at 15 to 30° C. for 2 to 3 minutes. The samples were centrifuged at no more than 12,000×g for 15 minutes at 2 to 8° C. Following centrifugation, the mixture separated into a lower red, phenol-chloroform phase, an interphase, and a colorless upper aqueous phase. RNA remained exclusively in the aqueous phase.

RNA precipitation: The aqueous phase was transferred to a fresh tube. The RNA was precipitated from the aqueous phase by mixing with isopropyl alcohol (Fluka). 0.5 ml of isopropyl alcohol was added for every 1 ml of trizol reagent which was added for homogenization initially. The samples were incubated at 15 to 30° C. for 10 minutes and centrifuged at no more than 12,000×g for 10 minutes at 2 to 8° C.

RNA wash: The supernatant was removed. The RNA pellet was washed once with 75% ethanol, using at least 1 ml of 75% ethanol for every 1 ml of trizol reagent, which was added for the homogenization initially. The sample was mixed by vortexing and centrifuged at no more than 7,500×g for 5 minutes at 2 to 8° C.

Re-dissolving the RNA: The supernatant was removed, and then the RNA pellet was dried. The RNA was dissolved in RNase-free water, and incubated for 10 minutes at 55 to 60° C. The RNA can be stored at −70° C.

Cell Lines

Human tumor cell lines (MCF-7, CL1-5, HT-29, Caco-2), human umbilical vascular endothelial cells (HUVEC), and human dermal fibroblasts (HDF) were tested for sensitivity on *Angelicae sinensis* extracts, ligustilide, n-butylidenephthalide and its derivatives in vitro. The DBTRG-05MG, BCM, HL-60 and J5 cells were grown in RPMI-1640 medium containing 10% fetal calf serum and 100 ng/ml penicillin and 100 ng/ml streptomycin at 37° C. in a humidified atmosphere with 5% $CO_2$. The G5T/VGH, RG2, Ni 8, SVEC and Balb/3T3 cells were cultured in DMEM with 10% fetal calf serum and 100 ng/ml penicillin and 100 ng/ml streptomycin at 37° C. in 5% $CO_2$. Mycoplasma infection of the culture cells was excluded by PCR screening methods before each experiment.

EXAMPLE 1

Analysis of Cell Cytotoxicity

The effects on cell viability after the treatments with different concentrations of the *Angelicae sinensis* extracts or the active components purified therefrom were evaluated by modified MTT assay in triplicate. Briefly, the cells ($5\times10^3$) were incubated into 96-well plates containing 100 μl of a growth medium. The cells were permitted to adhere for 24 hours, then treated with 100 μl of the herbal extracts or the active components dissolved in the medium. The control contained DMSO of <0.02% (v/v). After 24, 48 and 72 h incubation, the drug-containing medium was replaced by 50 μl of fresh medium, and cells in each well were incubated in 50 μl of 400 μg/ml MTT for 6-8 h. The medium and MTT were removed later and 100 μl of DMSO was added to each well and to the control, to dissolve the soluble components. Absorbance at 550 nm of the solutions was measured with MRX Microtiter Plate Luminometer (DYNEX, USA). The absorbance of untreated cells was considered as 100%. To evaluate the effects of the extracts or the active components on cell growth rate of GBM cells, $5\times10^3$ exponentially growing cells were treated with different concentrations for 24, 48, or 72 h. The cytotoxicity of each test substance was determined as an IC50 value, which represents the drug concentration required to cause 50% inhibition. All experiments in this study were performed in triplicate.

TABLE 1

Cytotoxicity (IC50) of the different *Angelicae sinensis* organic solvent extracts, BP and its derivatives on different cells lines.

| | Cytotoxicity, $IC_{50}$ | | | | |
|---|---|---|---|---|---|
| | Normal Cells | | Cancer cells | | |
| | HUVEC | HDF | Caco-2 | MCF-7 | RG2 |
| Extract (μg/ml) | | | | | |
| AS-A | 91.85 | >100 | >100 | 92.06 | 6.83 |
| AS-C | 44.19 | 85.08 | 51.17 | >100 | 7.22 |
| AS-H | >100 | 66.55 | >100 | 62.42 | 30.49 |
| BP | >100 | 300 | >20 | >20 | 1.4 |
| | (>532 μM) | (1596 μM) | (>106 μM) | (>106 μM) | (7.45 μM) |
| BP-E form | >100 | >100 | | | >20 |
| | (>532 μM) | (>532 μM) | | | (>106 μM) |
| BP-Z form | >100 | 65.25 | | | >20 |
| | (>532 μM) | (347 μM) | | | (>106 μM) |

HUVEC: Human umbilical vascular endothelial cells
HDF: Human dermal fibroblasts
Caco-2: Human colon adenocarcinoma
MCF-7: Human breast carcinoma
RG2: Rat malignant glioma

TABLE 2

Cytotoxicity ($IC_{50}$) of the organic solvent extracts of *Angelicae sinensis*, and BP on different cell lines.

| | AS-A (μg/ml) | AS-C (μg/ml) | AS-H (μg/ml) | BP (μg/ml) |
|---|---|---|---|---|
| A549 | 90-110 | | | 8-12 (42.6-63.8 μM) |
| AT12 | 100 | | | 10-15 (53.2-79.8 μM) |
| J5 | 70-90 | | | 15-20 (79.8-106.4 μM) |
| HCT15 | 80-100 | | | 25-30 (133.0-160.0 μM) |
| HT-29 | 21-94 | 20 | 30 | 15-97 (79.8-516.0 μM) |
| CL1-5 | 29 | 22 | 28 | >100 (>532 μM) |
| DBTRG-05MG | 40-110 | 44 | >400 | 7-10 (37.2-53.2 μM) |
| G5T/VGH | 50-223 | 46-60 | | |
| N18 | 111 | 35 | | |
| BCM | 300 | 142 | >400 | |
| HL-60 | 367 | 173 | | |
| RG2 | 35 | 30 | | 1.4 (7.45 μM) |
| SVEC | 76 | 86 | | |
| Balb/3T3 | 38 | >400 | >400 | >300 (>1596 μM) |

A549, AT12: Human lung adenocarcinoma cell lines (AT12 and A549 are taxol-resistant subclones)
J5: Human hepatoma cell line
HCT15: Human colon adenocarcinoma cell line
HT-29: Human colon adenocarcinoma cell line
CL1-5: Human lung adenocarcinoma
DBTRG-05MG: Human glioblastoma multiform cell line
G5T/VGH: Human glioblastoma multiform cell line
N18: Neuroblastoma
BCM: Human breast carcinoma
HL-60: Human promyelocytic leukemic cell
RG2: Rat maglinant glioma
SVEC: SV40 transformed mouse lymph node endothelial cell
Balb/3T3: Mouse fibroblast cell

TABLE 3

Test results of ETS-1, MMP-2, cell migration and tube formation of HUVEC Inhibition

| | | RT-PCR | | | Tube |
|---|---|---|---|---|---|
| | | ETS-1 | MMP-2 | Migration | Formation |
| Extract (μg/ml) | AS-A | 1 | 1 | 30 | 30 |
| | AS-C | 30 | 30 | 1 | 10 |
| | AS-H | 100 | 100 | 30 | 10 |
| | BP | 53.13 | 159.4 | | 531.3 |
| | | (282.6 μM) | (847.9 μM) | | (2826 μM) |
| | BP-E form | 159.4 | — | | — |
| | BP-Z form | 159.4 | 531.3 | | 159.4 |

Both the n-butylidenephthalide (BP) and the *Angelicae sinensis* extracts (AS-A, AS-C, AS-H,) generally displayed a lower value of $IC_{50}$ to a number of human tumor cell lines (Table 1 and Table 2) in comparison with the normal cells (HUVEC and HDF). BP, in particular, exhibited strong cytotoxic effect on human brain tumor cells. BP was also cytotoxic to two taxol-resistant human lung adenocarcinoma cells, a human hepatoma cell and two human colon adenocarcinoma cells.

The $IC_{50}$ of AS-C and BP to brain tumor cell lines were 35~60 μg/ml and 1.4~10 μg/ml, respectively, while those to the normal cell line (HDF) were 85~300 μg/ml, (p<0.0001).

Among the normal cells, the vascular endothelial cells ($IC_{50}$=44.2±0.1 μg/ml) were more sensitive than fibroblast cells ($IC_{50}$=85.1 μg/ml) to AS-C (p<0.05).

The inhibition effects of carmustin (BCNU) and Taxol were also tested and compared. The results showed that GBM tumors were not sensitive to carmustin ($IC_{50}$>100 μg/ml) but DBTRG-05MG and G5T/VGH GBM cells were sensitive to Taxol ($IC_{50}$=61.0±3.3 μg/ml and $IC_{50}$<0.1 μg/ml, respectively). However, Taxol induced a very high cytotoxicity ($IC_{50}$<0.1 μg/ml), which is much greater than that induced by AS-C and BP, in vascular endothelia cells. After treatment with AS-C or BP, the GBM cells (DBTRG-05MG) were seen to be detached and floating in the media at different points of time within a 72-hour period of observation. The extent of GBM cell detachment and flotation was found to increase with time, and with the increase in dosage (in the case of BP when an observation was made at 3 hours).

The GBM cell detachment and flotation after treatment with AS-C or BP, can be attributed to morphology change in the tumor cells. In the above experiment, BCNU (carmustin) was used as the system control.

EXAMPLE 2

AS-C and BP Enhance the Cell Cycle Arrest at G0/G1 Phase in GBM Cells

Brain tumor cell lines DBTRG-05MG and G5T/VGH were cultured in the growth medium with a diluent. For each test and control, DMSO was added, and the content is less than 0.02% (v/v). For the AS-C and BP treatment, 70 μg/ml of AS-C and 400 μM of BP were added, respectively. All were cultured for 48 hours. The analysis of cell cycle distribution was performed by DNA staining with propidium iodide (PI). Briefly, $2\times10^6$ adherent cells were detached by trypsinization. The detached cells and the floating dead cells were centrifuged and washed twice with 10 ml of cold 1×PBS (Life Technologies, Inc.). Supernatant was aspirated, cells were re-suspended in 0.8 ml of 1×PBS, and then 200 μl of PI solution (50 μg/ml PI+0.05 mg/ml RNase A; Sigma Chemical Co.) was added, and the cells were refrigerated at 4° C. overnight. The cells were incubated while protected from light at room temperature for at least 2 h before DNA analysis. After staining, DNA was detected and quantified on 20,000 total cells using a FACScan (Becton Dickinson Immunocytometry Systems, San Jose, Calif., USA) and CellQuest analysis software. The G0/G1 phases were gated in M1 (×2); G2/M phases were gated in M2 (×2); the total cells were gated in M3; S phase was M3−(M1(×2)+M2(×2)); Sub G1 phase (apoptosis cells) was gated in M4.

Figure 1B:
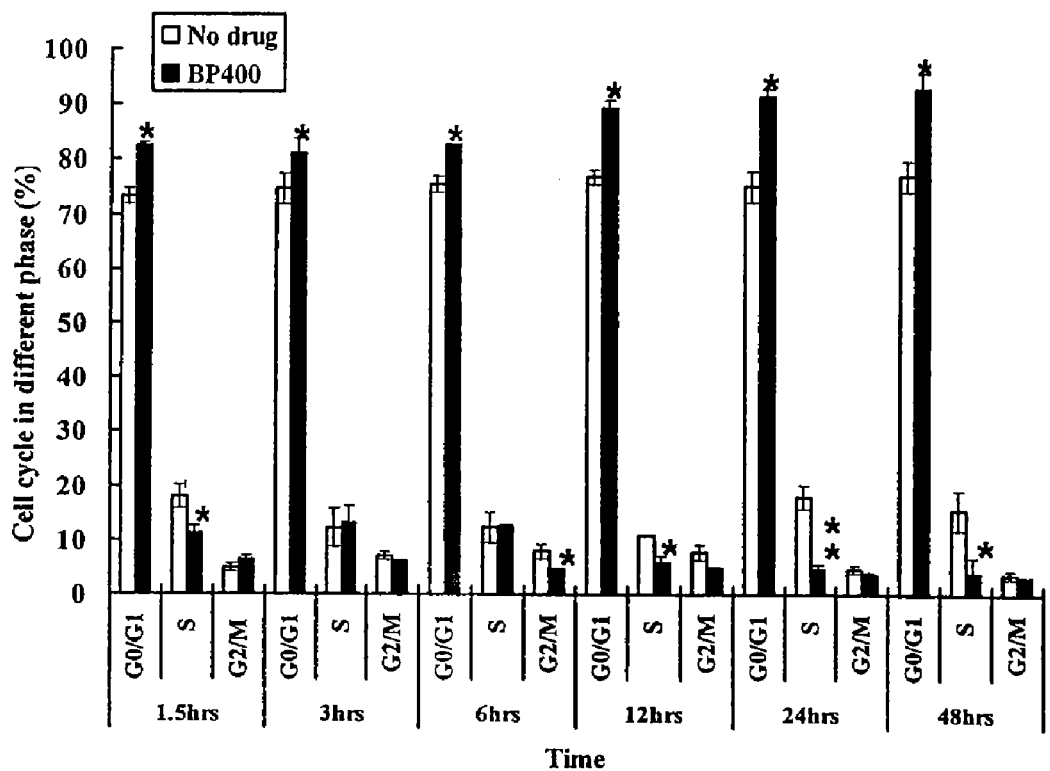
FIG. 1b provides the results of the cell cycle analysis, which demonstrates that the treatment with 400 μM BP enhanced cell cycle accumulation at G0/G1 phase (>90%) in GBM cells (DBTRG-05MG) (*$p<0.05$, **$p<0.005$) with concurrent decrease in S phase.

The cell cycle analysis demonstrated that both 70 μg/ml of AS-C and 400 μM of BP enhanced the cell cycle accumulation at G0/G1 phase (>90%) in GBM cells. FIGS. 1a and 1b showed that both AS-C and BP enhanced a significant G0/G1 phase arrest with a concurrent decrease of S phase after treatment for 12 hours to 48 hours ($p<0.05$, $p<0.005$).

EXAMPLE 3

AS-C and BP Induce GBM Cells Apoptosis

Apoptotic cell death was analyzed using In Situ Cell Death Detection Kit, POD (Roche, Germany). Changes in DNA chromatin morphologic features were used for quantification. The procedures were performed in accordance with the manufacturer's instructions. Briefly, cells were cultured on culture dish and analyzed 72 hours after treatment with AS-C (70 μg/ml) and BP (5~800 μg/ml), respectively. In AS-C and BP-treated groups, the suspended cells were collected. In the control group, adherent and floating cells were collected. Then, the cells were fixed with 3.7% formaldehyde at room temperature for 15 min. on saline coated slides, washed once in 1×PBS, and incubated in cold permeabilization solution (0.1% Triton X-100+0.1% sodium citrate) after reducing activity of endogenous peroxidase with 3% $H_2O_2$. The cells were washed with 1×PBS again, and incubated with terminal deoxynucleotidyl transferase (TdT)-mediated dUTP nicks labeling (TUNEL) reaction mixture for 60 minutes at 37° C. Then, the cells were washed with 1×PBS, counterstained with propidium iodide (PI) for cell counting. For quantification of apoptosis, the results were viewed under fluorescence microscopy (Nikon, Kawasaki, Japan).

Figure 2:
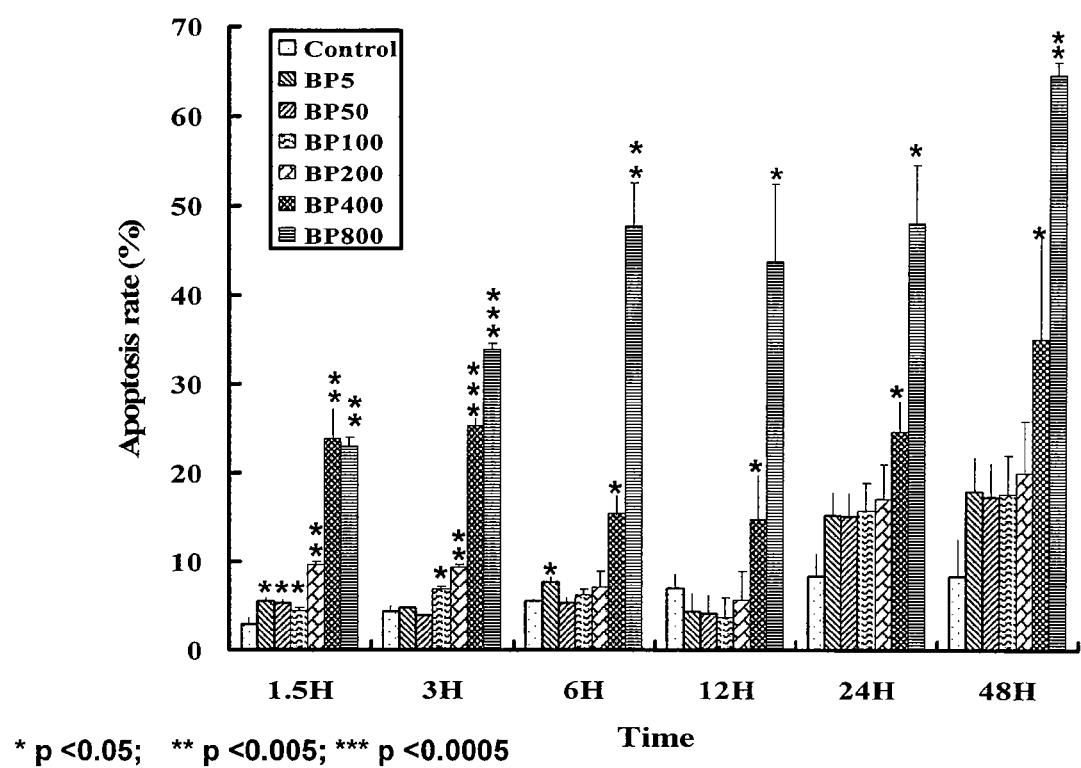
FIG. 2 shows the effect of BP (n-butylidenephthalide) of 5 to 800 μM, in inducing GBM tumor cell (DBTRG-05MG) apoptosis, as assessed by TUNEL method, using propidium iodide as a counter staining (*$p<0.05$,  $p<0.005$, * $p<0.0005$).

When compared to untreated cells, almost all detached GBM cells in the AS-C and BP-treated groups were found to have undergone apoptosis. The apoptotic cells with AS-C treatment were detected by fluorescence microscopy (400×), with In Situ TUNEL staining and propidium iodide cell counterstaining, and observed under light field. Likewise, BP induced apoptosis in GBM cells was assessed by TUNEL method and using propidium iodide as a counter stain. The GBM cells were exposed to BP (5 to 800 μM) for 48 hours before assessment. The results were shown in FIG. 2. It was found that as compared to the untreated cells (control), the apoptosis rates of GBM cells in the BP treatment group, were much higher.

EXAMPLE 4

AS-C and BP Induce Apoptosis through the Activation of Multiple Pathways

Western Blot Analysis of Apoptosis Molecules

Figure 3A:
FIGS. 3a-3c provide the results of the analyses of apoptosis pathways induced by AS-C, 70 μg/ml (wherein the DBTRG-05MG cell line was used.)

DBTRG-05MG cells (human GBM cells) were treated with AS-C (70 μg/ml) for 0, 6, 12, 24 and 48 hours. In another test, DBTRG-05MG cells were treated with BP (400 μM) for 0, 1.5, 3, 6, 12, 24 and 48 hours. The cell pellets were re-suspended in lysis buffer (10 nM Tris-HCl, pH 7.5, 1 mM EGTA, 0.5% CHAPS, 10% (v/v) glycerol, 5 mM β-2-mercaptoethanol and 0.1 mM phenylmethylsulfonyl fluoride) and incubated on ice for 30 min, and then centrifuged at 13000× rpm at 4° C. for 20 minutes. The protein concentration of whole cell lysates was measured with BCA protein assay kit (Pierce, Rockford, Ill.) following the manufacturer's instructions. The cell lysates (20 μg/lane) were electrophoresed on 10-12% SDS-PAGE (Bio-Rad, Hercules, Calif.). Proteins were transferred to polyvinyldenefluoride (PVDF) membranes (Amersham Lifesciences, Piscataway, N.J.). The membranes were masked for 1 hour at room temperature with 5% skim milk as the blocking agent, and incubated with the respective antibodies of Fas (FL-335), Fas-L (C-178), caspase 3 (H-277), caspase 8 (H-134), caspase 9 (H-170), Bax (B-9), p16 (F-12), p21 (F-5), p53 (DO-1; 1/100 dilution) (Santa Cruz Biotechnology Inc., CA, U.S.A.), phospho-p53 (Ser15; 1/2000 dilution) and phospho-Rb (Ser795; 1/2000 dilution) (Cell Signaling Technology, MA, USA) for 2 hours at room temperature. Antibody recognition was detected, by incubating the membranes with the respective anti-mouse, anti-rabbit, anti-goat IgG secondary antibodies (1/1000 dilution; Santa Cruz Biotechnology Inc., CA, U.S.A.) conjugated to horseradish peroxidase, for 1 hour at room temperature, and visualized with the ECL Plus chemiluminescence system (Amersham, Arlington Heights, Ill.). For system control, SDS-PAGE gels, for every test sample, were prepared in duplicate, containing the same amount of protein; and the control gel was stained with coomassie blue. The other gel was used for Western Blot analysis. The intensity of the bands was analyzed by densitometry with a GS-800 Calibrated Imaging Densitometer (Quantity One 4.0.3 software; Bio-Rad). The results showed that AS-C significantly increased Fas expression of GBM cells (1 to 159 fold) but not Fas-L expression. In addition, the activation of the death receptor-induced apoptosis-related caspases-8 was monitored. The results indicated that the amount of procaspase-8 was only slightly increased at 6 h after AS-C treatment, whereas the amount of the activated caspase-8 was greatly increased at 6 h after AS-C treatment (see FIG. 3a).

Figure 3B:
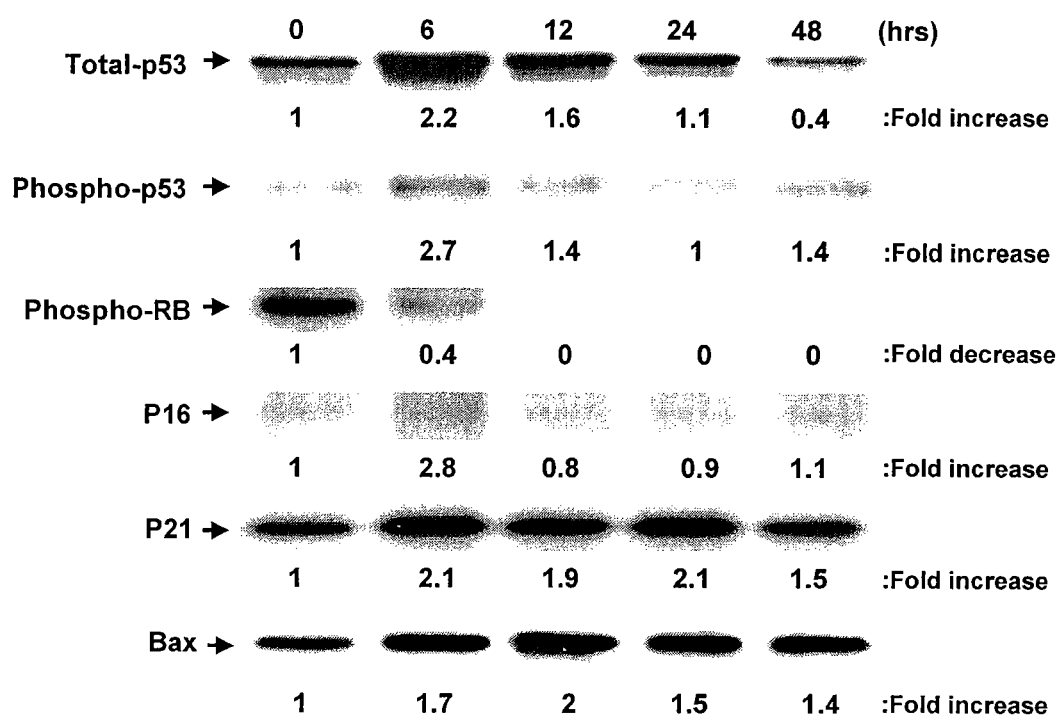

The phosphorylations of p53 and Rb proteins were monitored and the results showed the AS-C increased phosphorylated p53 protein at 6 h after treatment. Furthermore, the amount of total p53 protein was increased as well at 6 h and then gradually decreased. However, phosphorylated Rb protein was seen to decrease at 6 h, and became undetectable at 12 h after AS-C treatment. These results indicated that AS-C could trigger the cell cycle checkpoint machinery. The amounts of p16, p21 and Bax in AS-C treated GBM cells were consequently measured and all of these three proteins were found to increase after treatment with AS-C (see FIG. 3b).

Figure 3C:
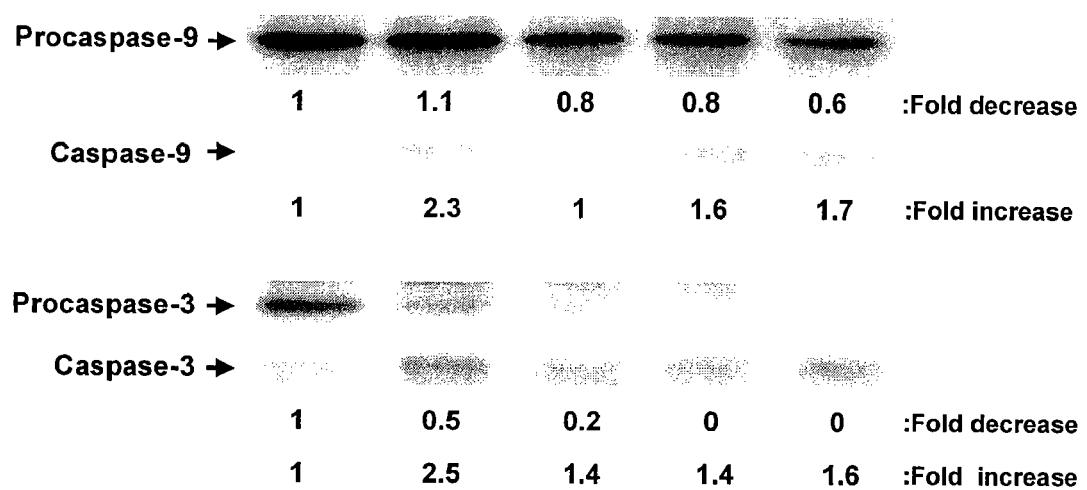

Finally, the activations of procaspase-9 and procaspase-3 were also determined. Both procaspase-9 and procaspase-3 were highly activated at 6 h after AS-C treatment (FIG. 3c).

Figure 3D:
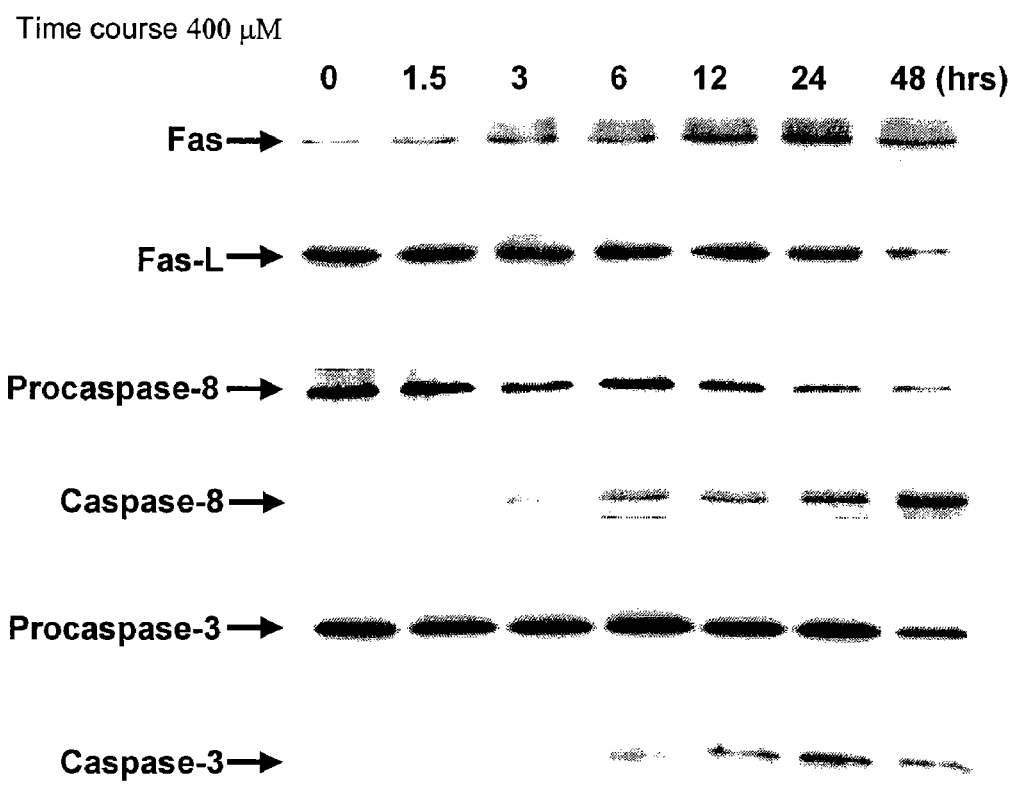
FIGS. 3d-3g provide the results of the analyses of apoptosis pathways induced by BP, 400 μM (wherein the DBTRG-05MG cell line was used.)

In the case of BP, the results showed that BP 400 µM greatly increased the expression of Fas (from 5.2 times at 1.5 h to 27.9 times at 48 h), while suppressing the expression of the Fas Ligand on the GBM cells (see FIG. 3d).

It is also observed that BP enhanced the activation of caspase 8, which was increased to 137.9 by the 48 h, while procaspase 8 declined (see FIG. 3d).

Figure 3E:
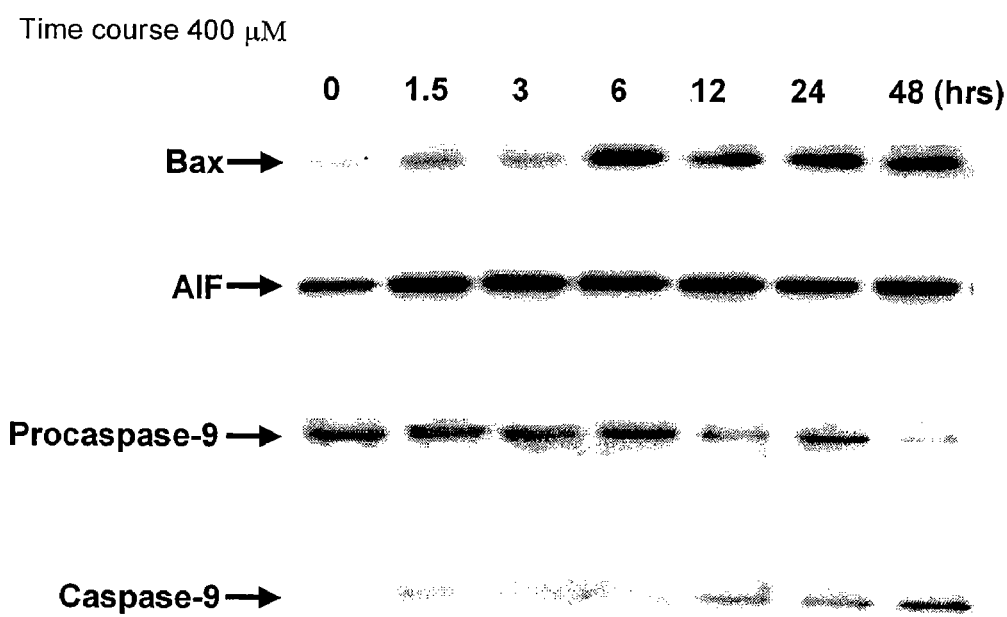

The study of the role of mitochondrial pathway in BP-induced apoptosis showed that BP induced Bax and AIF expression, which increased to 16 times and 2.4 times respectively, by the 48 h, and activated caspase-9 by 25.8 times at the 48 h while procaspase-9 declined (see FIG. 3e). Caspase-3 was also observed to increase while procaspase-3 declined (FIG. 3d).

Figure 3F:
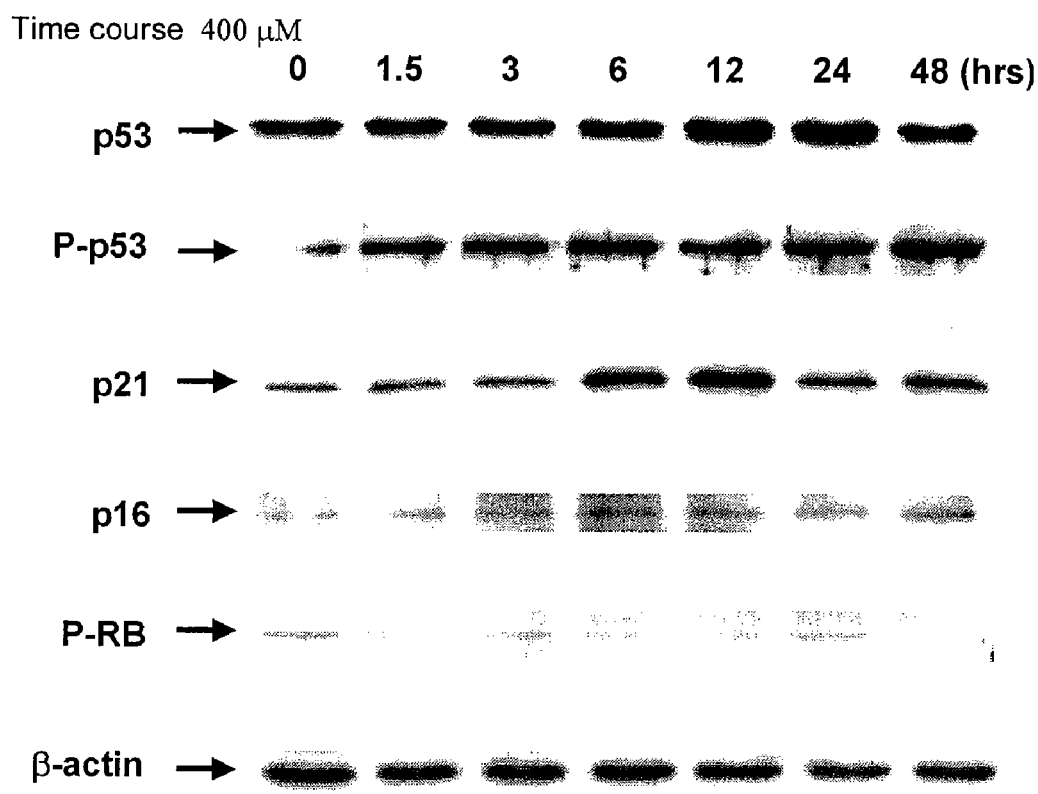
Figure 3G:
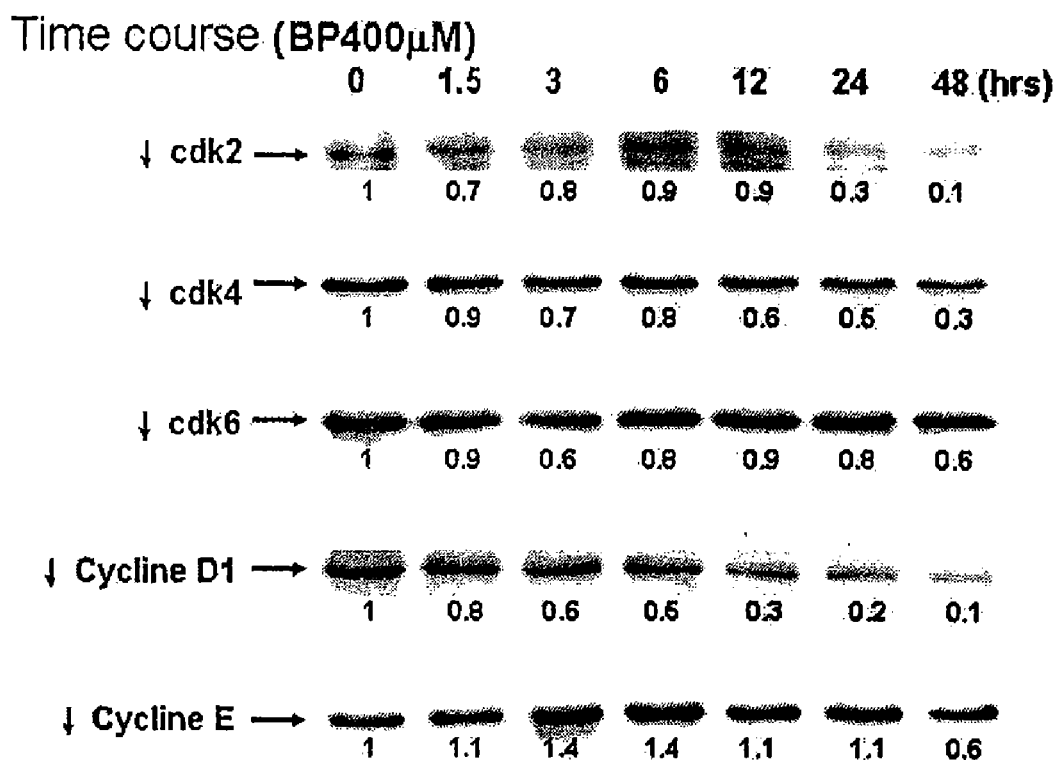

The study of the role of cell cycle pathway in BP-induced apoptosis showed that BP increased p53, p21 and p16 expression by 1.4, 2.3 and 3.1 times respectively at 48 h. It also increased p53 phosphorylation by 5.2 times at 1.5 h and 9.2 times at 48 h, but decreased Rb phosphorylation by 0.2 times at 48 h (FIG. 3f). Beta-actin was used as an internal control in this study. In FIG. 3g, BP was seen to decrease also cdk2, cdk4, cdk6 cyclins D1 and cycline E.

In conclusion, we theorize a schematic model of the apoptosis signal transduction pathways induced by BP stress, which consists of death receptor, mitochondrial and cell cycle pathways.

EXAMPLE 5

Animal Studies

The RG2 cells (rat GBM) and DBTRG-05MG cells (human GBM) were used in animal experiments to monitor the anti-tumor activities of AS-C and BP. Male F344 rat (230-260 g) and male Foxn1 nu/nu mice (10-12 weeks) were obtained from National Laboratory Animal Center (Taipei, Taiwan). All procedures were performed in compliance with the Standard Operation Procedures of the Laboratory Animal Center of Tzu Chi University (Hualien, Taiwan). Animals were kept under pathogen-free conditions and fed a standard laboratory diet. The DBTRG-05MG cells (human GBM) and RG2 cells (rat GBM) were prepared for nude mice xenografts and rat allogenics, respectively.

For AS-C Treated Group

Experiment 1—Effect of AS-C administered by subcutaneous injection on the survival rate and tumor size of rats bearing subcutaneous GBM tumor Syngeneic F344 rats in two groups (6/group) were implanted subcutaneously on the back with $1 \times 10^6$ RG2 cells. The animals were administered by subcutaneous injection either with AS-C (500 mg/kg/day) (treatment group), or with the vehicle (50 mg/ml propylene glycol and 100 mg/ml Tween-80 in distilled water; Standard Chem. & Pharm., Tainan, Taiwan) (control group), at a spot distant from the inoculated tumor sites (>2 cm), on day 3, 6 and 9, after tumor cell implantation. Tumor sizes were measured using a caliper and the volume was calculated as L×H×W×0.52. The animals were sacrificed when tumor volume exceeded 25 cm$^3$ and the day of sacrifice was assumed as the final survival day for the animals.

Figure 4:
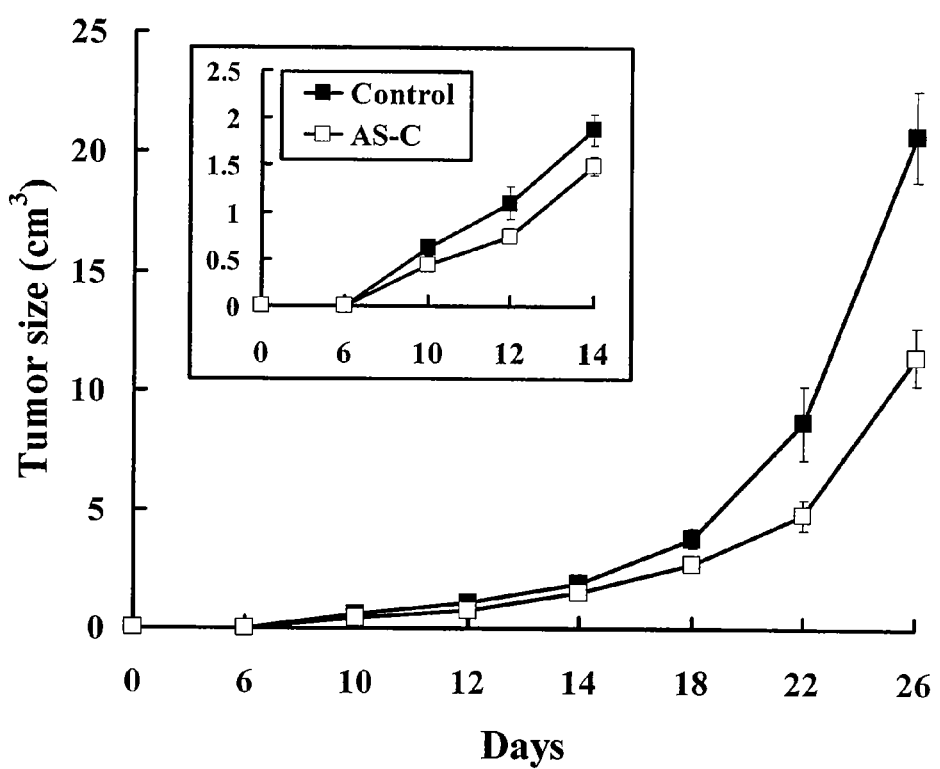
FIG. 4 shows the inhibitory effect of the AS-C treatment (500 mg/kg) on the tumor sizes in mice bearing subcutaneous GBM tumors (RG-2) ($p<0.05$).
Figure 5:
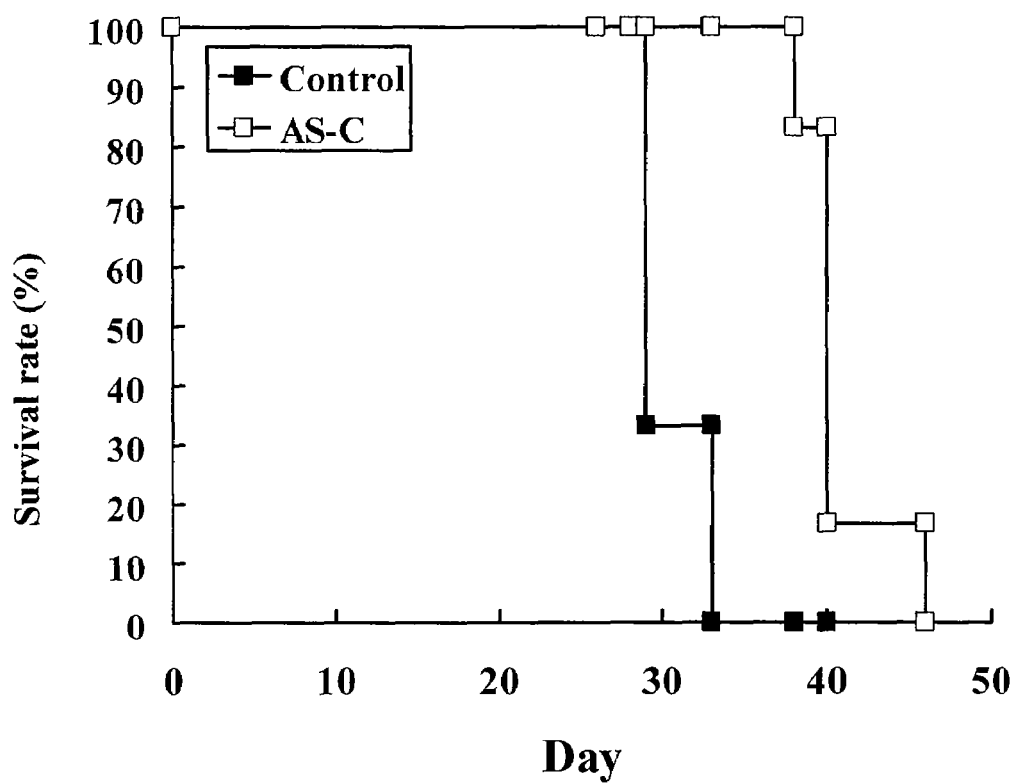
FIG. 5 shows that the survival rate of the AS-C treated mice (dose—500 mg/kg) was significantly prolonged as compared with the control group ($p<0.0001$), wherein the DBTRG-05MG cell line was used.

The results showed that AS-C treatment had a significant inhibitory effect on tumor growth when compared with the untreated (control) group (p<0.05) (FIG. 4). The average tumor size at day 26 was 20.7±1.5 cm$^3$ for the control group and 11.5±0.7 cm$^3$ for the treatment group, respectively. Survival of rats in the AS-C treated group was significantly prolonged, compared with those in the control group (40±2.7 days vs 30±2.1; p<0.0001) (FIG. 5).

With a dose of 500 mg/kg subcutaneous injection of AS-C, no drug related toxicities were observed in the rats as evidenced by the results of the body weights and histological analysis of the vital organs.

Experiment 2—Comparative effects of AS-C administered by subcutaneous injection and by intra-peritoneal injection on the tumor size of mice bearing subcutaneous human GBM tumor Nude mice, in two groups (6/group), were implanted s.c. with $5 \times 10^6$ DBTRG-05MG cells, and administered with AS-C (i.p. 500 mg/kg/day), AS-C (s.c. 500 mg/kg/day) or vehicle (s.c.) on day 5 after tumor cell implantation. Tumor sizes were measured using a caliper and the volume was calculated as L×H×W×0.52. The animals were sacrificed when tumor volume exceeded 1000 mm$^3$ in mice, and the day of sacrifice was assumed as the final survival day for the animals.

Figure 7:
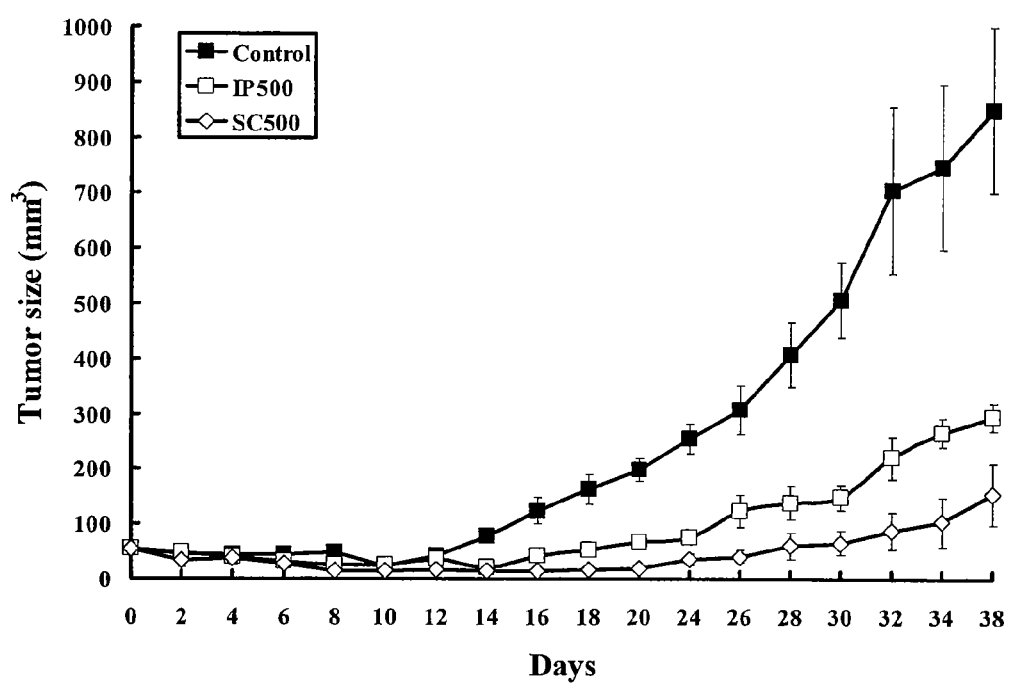
FIG. 7 shows the inhibitory effect of the AS-C treatment (500 mg/kg by intra-peritoneal or subcutaneous administration) on the xenograft tumor growth of mice ($p<0.005$), wherein the DBTRG-05MG cell line was used.

The results showed that there were significant suppressions of tumor growth in the AS-C i.p. (500 mg/kg) and AS-C s.c. (500 mg/kg) treated groups compared with the untreated group (p<0.005). The mean values of tumor sizes at day 38 were 849.9±150.1 mm$^3$ in the control group, 295.5±25.3 mm$_3$ in AS-C i.p. (500 mg/kg) treated group and 155.1±56.4 mm$^3$ in AS-C s.c. (500 mg/kg) treated group. The results were shown in FIG. 7.

Experiment 3—Effect of AS-C administered by subcutaneous injection, on the tumor size of rats bearing in situ GBM tumor (intra-cranial allogenic GBM).

The cytotoxic effect of AS-C on in situ tumor was determined with RG2 cells. Syngeneic rats in two groups (6/group), were implanted i.c. (striatum) with $5 \times 10^4$ RG2 cells, and treated with AS-C (500 mg/kg/day) or vehicle s.c. at day 4, 5, 6, 7 and 8 after tumor cell implantation. Tumor volumes were measured and calculated by 3-T unit MRI (General Electric, Wisconsin, USA) with echo-planar imaging capability (Signa LX 3.8, General Electric, Wisconsin, USA) in Buddhist Tzu Chi General Hospital (Hualien, Taiwan). Briefly, rats were anesthetized with chloral hydrate (400 mg/ml, 1 ml/100 g). Functional MRI scanning was conducted with a fast spin echo, echo-planar acquisition sequence in which the repetition time was 6000 msec, the echo time was 102 msec, the matrix image was 256 by 256, the field of view was 5 by 5 cm, and the in-plane resolution was 80 µm. Twenty slices, each 1.5 mm thick, were obtained every 19.5 seconds for 6.5 minutes for each rat.

Figure 6:
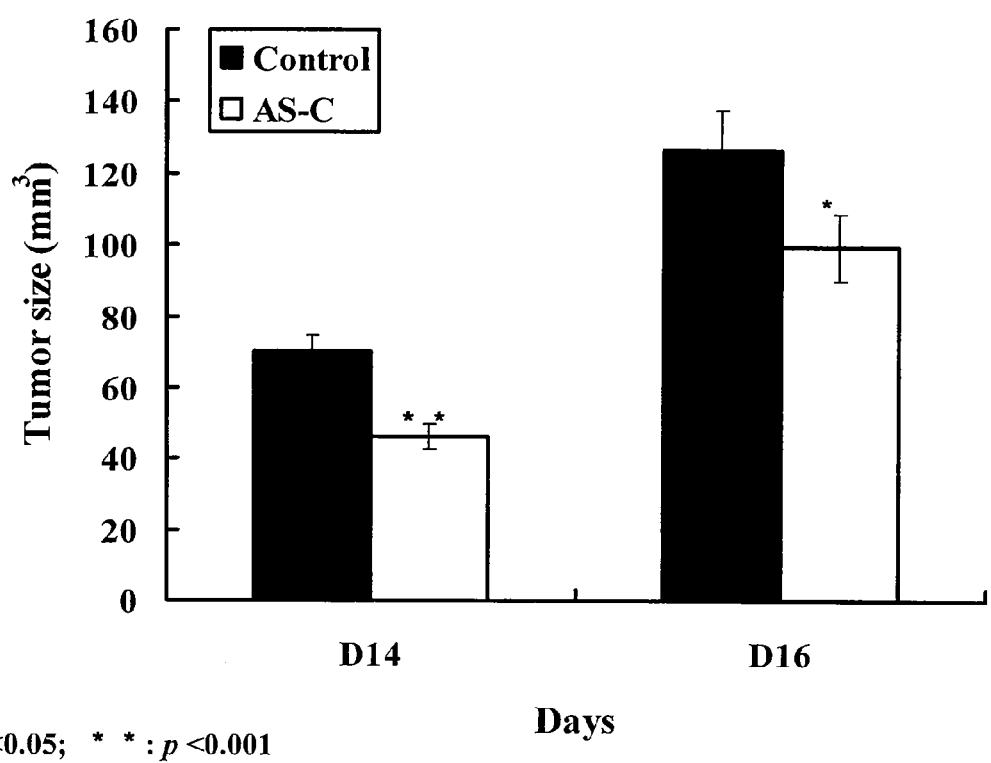
FIG. 6 shows the inhibitory effect of AS-C treatment (500 mg/kg) on the growth of in situ GBM tumor (RG2) volume on rats (* $p<0.05$, ** $p<0.001$).

Significant declines of tumor volume in the treated group were observed in the MRI image data, compared with the untreated group (p<0.05) (FIG. 6). The mean tumor volumes at day 14 and day 16 were 70±4.8 mm$^3$ and 126.4±11.1 mm$^3$ in the control group versus 46.2±3.6 mm$^3$ and 99.5±9.5 mm$^3$ in AS-C treated group.

Experiment 4—Cytotoxicities of AS-C administered by subcutaneous injection, on the tumor size of mice bearing xenograft human GBM tumor In this experiment, the tumor was allowed to grow to a larger size to simulate a clinical condition where surgical removal of tumor was not an acceptable option.

As described above, DBTRG-05 MG cells ($5\times10^6$) were implanted s.c. on the backs of nude mice. The tumor-bearing mice were treated with single dose of AS-C (500 mg/kg) or vehicle (s.c.) only when the tumor volumes were >250 $mm^3$. The mice were sacrificed to determine the cytotoxicities in tumors by H&E tissue staining at day 10 after treatment of AS-C. The tissue sections were observed and photographed under a light microscope at magnifications of 50× and 400×.

The photographs of histology analysis showed that AS-C had induced a nucleic degradation, a cavity cytosol and tumor cell death in the tumor cell mass. In contrast, the control tumor were growing very well and the cytotoxic effects as seen in the AS-C treated group, were not found in the tumor mass.

For BP Treated Group

Experiment 1—Effects of BP on intracranial (i.c.) rat allogenics GBM tumors in F344 male rat.

The rats in two groups (6/group) were implanted i.c. (striatum) with $5\times10^4$ RG2 cells, and randomly treated with BP (300 mg/kg/day) or vehicle s.c. in the hind flank region after tumor cell implantation at day 4, 5, 6, 7 and 8 for five dosages. Tumor volume was measured and calculated by MRI. MRI was performed with a 3-T unit (General Electric, Wisconsin, USA) with echo-planar imaging capability (Signa LX 3.8, General Electric, Wisconsin, USA). Briefly, rats were anesthetized with chloral hydrate (400 mg/ml, 1 ml/100 g). Functional MRI scanning was conducted with a fast spin echo, echo-planar acquisition sequence in which the repetition time was 6000 msec, the echo time was 102 msec, the matrix image was 256 by 256, the field of view was 5 by 5 cm, and the in-plane resolution was 80 μm. Twenty slices (1.5 mm thick each) were obtained every 19.5 seconds for 6.5 minutes for each rat. Finally, the whole tumor sizes ($mm^3$) were measured and calculated for each group.

Figure 8:
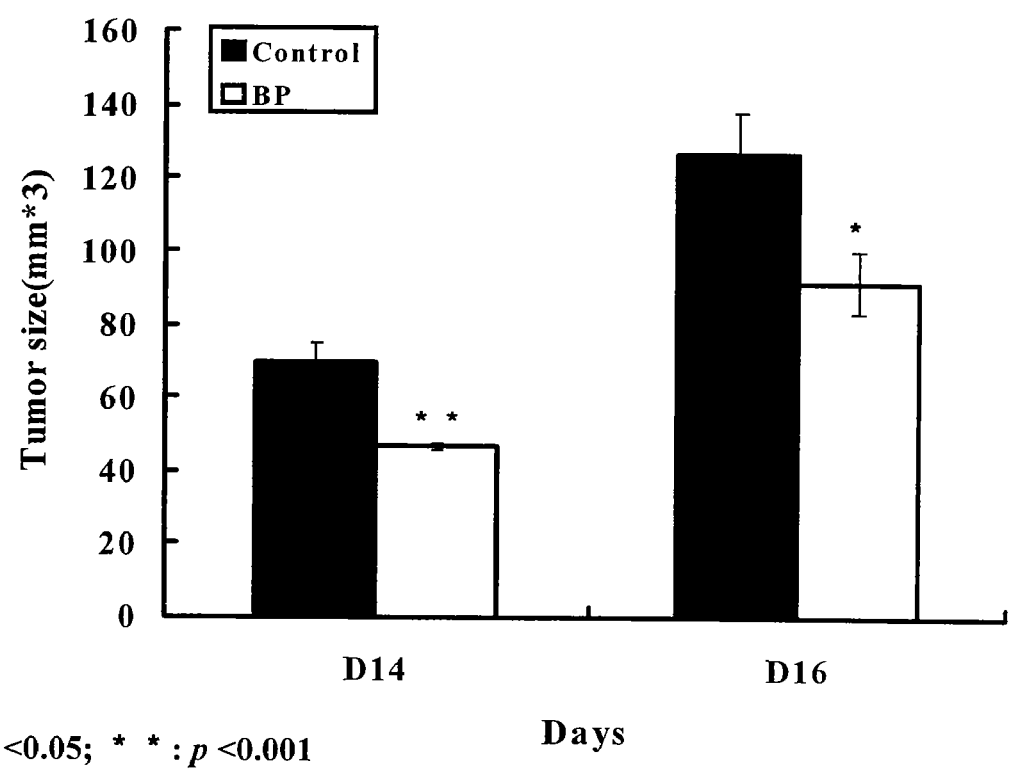
FIG. 8 shows the inhibitory effect of the BP treatment (300 mg/kg) on tumor volume of GBM in situ (RG2) on rats, which was calculated with MRI imaging using echo-planar imaging capability (* $p<0.05$, ** $p<0.001$).

The results indicated that there was a significant reduction of tumor volume in the BP treated group as compared with the untreated group ($p<0.05$), as calculated using MRI scanning and Echo-planar as described above (FIG. 8). Each column in FIG. 8 represents a mean±SE (*:$p<0.05$; **: $p<0.001$). The mean of tumor volumes at day 14 and day 16 were 69.9±4.81 mm3 and 126.43±11.07 $mm^3$ for the control group respectively; and 46.6±1.8 $mm^3$ and 91.68±8.3 $mm^3$ for the BP-treated group respectively. MRI image data showed that the tumor volume in situ of BP-treated group had a smaller region than control group.

Experiment 2: Effects of BP on supressing the growth of s.c. xenograft human GBM tumors in nude mice, and on the survival rate of the mice.

Animals (Foxn1 nude mice) in six groups (6/group) were implanted subcutaneously (s.c.) with $1\times10^6$ DBTRG-05MG cells, and randomly treated with BP s.c. (70, 150, 300, 500, 800 mg/kg/day) or vehicle s.c. at a site remote (>2 cm) from the incubated tumor after tumor cell implantation, at day 4, 5, 6, 7 and 8 for all five dosages. Tumor size was measured every 2 days and tumor volume was calculated. Animals were sacrificed when tumor exceeded 1000 $mm^3$. Tumor growth was monitored for 3 months for those not sacrificed. Survival rate was followed for up to 200 days.

Figure 9:
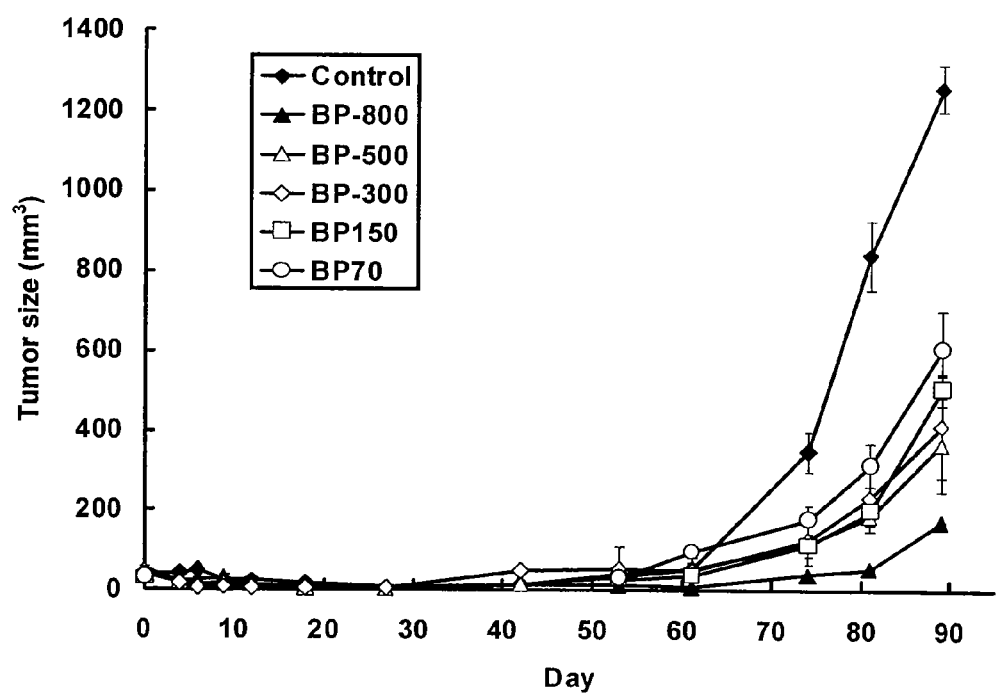
FIG. 9 shows the inhibitory effect of BP treatment, at different dosages (70 to 800 mg/kg), on xenograft tumor growth on mice ($p<0.005$), wherein the DBTRG-05MG cell line was used.

The results showed that there were significant suppressions of tumor growth in the BP-treated groups compared with the untreated group (FIG. 9; $p<0.005$ for the 300 mg/kg group), and the degree of tumor growth inhibition is dose dependent.

Figure 10:
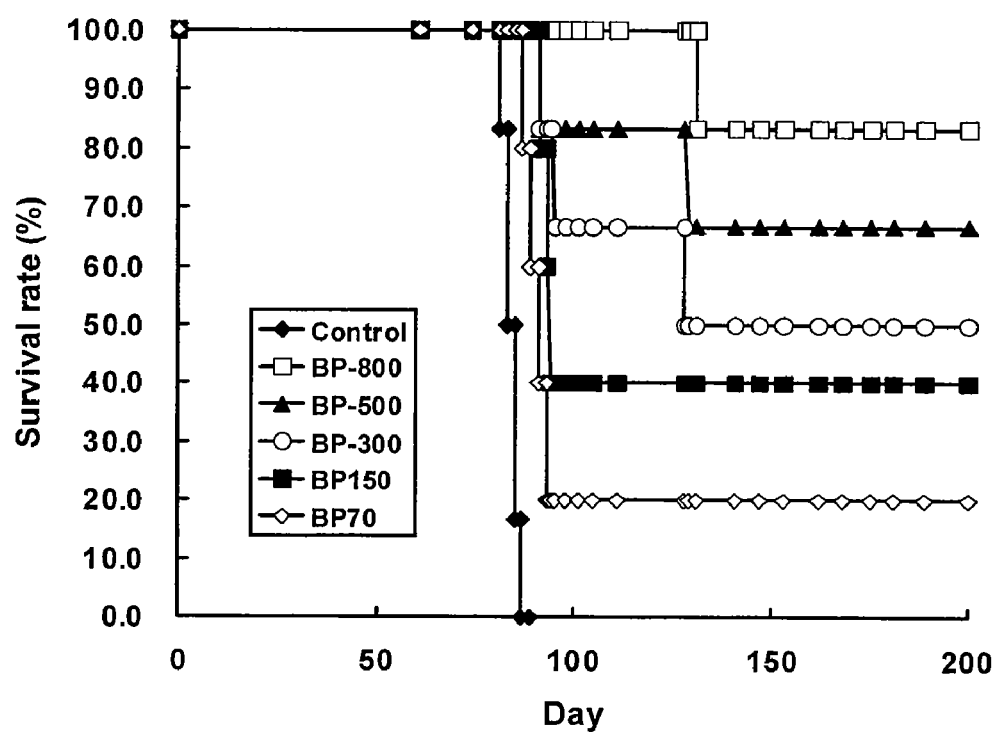
FIG. 10 shows the effect of BP treatment (70 to 800 mg/kg) on the prolongation of survival period of nude mice with xenograft tumor (subcutaneous DBTRG-05MG) ($p<0.001$).

Log-rank (Mantel-Cox) comparison of survival plots given in FIG. 10 indicated that the survival period of nude mice with xenograft subcutaneous human GBM was prolonged up to 200 days upon treatment with BP.

EXAMPLE 7

Effects of AS-C on Telomerase Activity of Human Malignant Tumor Cell

Assay for Telomerase Activity by Trap

The telomerase activity was measured by the modified telomere repeat amplification protocol (TRAP) assay as described in the literature. The pelleted cells were lysed with 200 μl of ice-cold lysis buffer (10 mM Tris-HCl, pH 7.5, 1 mM EGTA, 0.5% CHAPS, 10% [v/v] glycerol, 5 mM β-2-mercaptoethanol, and 0.1 mM phenylmethylsulfonyl fluoride) and incubated on ice for 30 minutes, and then centrifuged at 13,000×g at 4° C. for 20 minutes. The supernatant extracts were quantified for protein using a BCA Protein Assay Kit (Pierce, Ill., USA). TRAP assay was performed using a TRAPeze Telomerase Detection Kit (Intergen Co., Purchase, N.Y., USA) and the procedures were followed in accordance with the manufacturer's protocol. In brief, a volume of the extract containing 0.5 μg of protein was added to 50 μl of reaction mixtures containing 0.1 μg of substrate oligonucleotide (TS) primer SEQ ID NO:1 (5'-AATCCGTC-GAGCAGAGTT-3'), 0.1 μg of TSK1 template (internal control), 0.1 μg of reverse oligonucleotide primer (RP), 2 U of Takara Taq DNA polymerase (Takara Shuzo Co., Japan), 20 mM Tris-HCl, pH 8.3, 1.5 mM MgCl2, 63 mM KCl, 0.005% (v/v) Tween 20, 1 mM EGTA, 50 μM each of deoxynucleotide triphosphate (dNTPs), and 1.25 μCi of ($\gamma$32P) ATP, 3000 Ci/mmol (PerkinElmer Life Science, Boston, Mass., USA). The reaction mixtures were incubated at 94° C. for 2.5 minutes and then amplified for 30 cycles of polymerase chain reaction (PCR) amplification at 94° C. for 30 seconds, 59° C. for 30 seconds, and 72° C. for 90 seconds in a DNA thermal cycler (GeneAmp PCR System 2400, PerkinElmer Co., Norwalk, Conn., USA). The TRAP products were resolved by 12.5% (w/v) non-denaturing polyacrylamide gel electrophoresis (PAGE) in a buffer containing 54 mM Tris-HCl, pH 8.0, 54 mM boric acid, and 1.2 mM EDTA. The gel was dried on filter paper for 1 hour and exposed on the X-film (Bio-Max MR, Kodak Rochester, N.Y., USA) at −80° C. for 6 hours with an intensifying screen. The signal intensity of the TRAP assay DNA ladder products was quantified by the Bio-Profil Biolight imaging analysis software, V2000.01 (Vulber Lourmat, France) and compared.

Statistics

Data were expressed as the mean±SD or SE. Statistical significance was analyzed by Student's t-test. A p value of <0.05 was considered significant. Survival was compared by log-rank (Mantel-Cox) test. Median survival time was estimated from Kaplan-Meier analysis.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the appended claims.

What is claimed is:

1. A method for treating malignant glioblastoma in a subject in need thereof, comprising administering to the subject an active ingredient consisting essentially of n-butylidenephthalide alone.

2. The method according to claim 1, further comprising administering to the subject one or more chemotherapy drugs.

3. The method according to claim 1, wherein n-butylidenephthalide is administered via an oral, parenteral, intravenous (iv), intraperitoneal (ip), intravenous (iv), intramuscular (im), subcutaneous (sc), pulmonary, transdermal, buccal, nasal, sublingual, ocular, rectal or vaginal route.

* * * * *

```
                              SEQUENCE LISTING

<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 1
aatccgtcga gcagagtt                                                     18
```